United States Patent [19]

Fischer

[11] 4,248,218
[45] Feb. 3, 1981

[54] GAS ADMINISTRATION SCAVENGING MASK

[76] Inventor: Charles M. Fischer, 330 Twin Peaks La., Alamo, Calif. 94526

[21] Appl. No.: 944,713

[22] Filed: Sep. 22, 1978

[51] Int. Cl.³ ............................................. A61M 15/08
[52] U.S. Cl. ............................ 128/204.18; 128/207.18; 128/910
[58] Field of Search ............... 128/206, 207, 209, 210, 128/198, 203, 205, 208, 140 N, 139, 188, 204.18, 205.19, 205.24, 205.25, 207.13, 206.24, 207.11, 207.18

[56] References Cited

U.S. PATENT DOCUMENTS

| | | | |
|---|---|---|---|
| 1,896,716 | 2/1933 | McKesson | 128/206 X |
| 2,663,297 | 12/1953 | Turnberg | 128/206 |
| 4,015,598 | 4/1977 | Brown | 128/206 X |
| 4,151,843 | 5/1979 | Brekke et al. | 128/206 X |
| 4,156,426 | 5/1979 | Gold | 128/206 X |

*Primary Examiner*—Henry J. Recla
*Attorney, Agent, or Firm*—Allan J. Jacobson

[57] ABSTRACT

A scavenging mask apparatus for administering gas to a patient, the apparatus comprising a nasal cannula for delivering gas to the patient's nostrils, a tube connecting the cannula to a source of gas, a nosepiece adapted to fit over the nose and cannula, and a tube connecting the nosepiece to a source of vacuum. Gas exhaled through the patient's nostrils or escaping from the cannula is scavenged by the air flow in the nosepiece, thereby minimizing loss of gas to the environment. The nosepiece is also provided with a plurality of holes in the underside thereof to scavenge gas exhaled through the patient's mouth.

4 Claims, 7 Drawing Figures

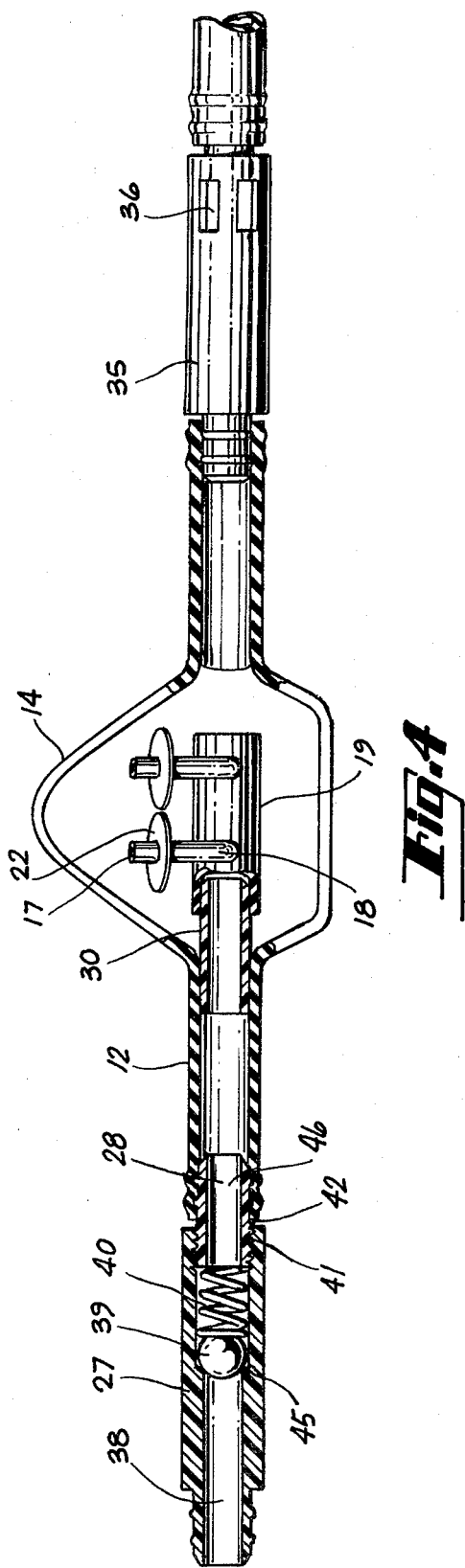
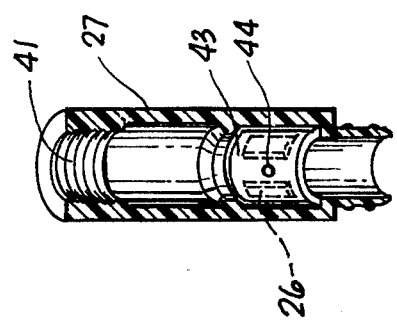
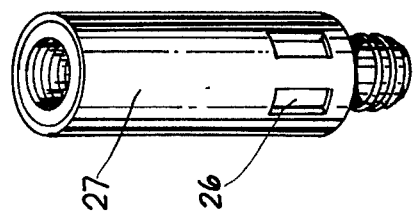

GAS ADMINISTRATION SCAVENGING MASK

FIELD OF THE INVENTION

This invention relates to an apparatus for administering gas to a patient, wherein vacuum means are used to scavenge exhaled and lost gas.

BACKGROUND OF THE INVENTION

Use of a gaseous analgesic such as nitrous oxide in dental work of a potentially painful nature has become widely accepted. Nitrous oxide reduces the patient's sensitivity to pain without rendering the patient unconscious. It can be administered nasally, leaving the mouth unobstructed and free for dental treatment.

Commonly, nitrous oxide is administered using a nasal inhaler, or nosepiece, secured over the patient's nose and connected through appropriate valves to a source of nitrous oxide. A typical example can be found in U.S. Pat. No. 3,889,671 to Baker. Many devices for administering nitrous oxide gas are available on the market. Some systems provide for a constant flow of gas; others are configured with pressure demand means so that gas is supplied only when the patient inhales. A nasal cannula can also be used, delivering the flow of gas directly into the patient's nostrils.

Available nitrous oxide masks and cannulas described above, release gas to the environment. In many systems, gas exhaled through the patient's nose is directly expelled from the nosepiece to the environment through a pressure relief valve. Also, since pressurized gas inside the nosepiece tends to lift the nosepiece away from the face, gas will leak through the facial seal at the rim of the nosepiece. Finally, gas is released to the environment by exhalation through the patient's mouth. Since very little gas is absorbed and retained by the patient, nearly all the gas administered to the patient is ultimately released into the room.

Release of nitrous oxide to the environment is undesirable for two reasons. First, there is the tendency for the dentist and other dental office personnel to become anesthetized. Second, exposure to nitrous oxide is an occupational hazard; studies have shown a probable correlation between routine long term exposure to nitrous oxide and certain serious diseases. Researchers suspect that the increased rate of spontaneous abortion among female anesthetists, increased incidence of birth defects among children born to anesthetists, and higher rates of cancer and disease of the liver and kidney, is related to chronic exposure to waste nitrous oxide. Clearly, a system for administering nitrous oxide without loss of gas to the environment is desirable.

Significant reduction in nitrous oxide levels in the dental operatory may be achieved by checking equipment for leaks and by using a gas scavenging system. Several types of scavenging masks are commercially available. One variety, described in U.S. Pat. No. 4,015,598 to Brown, includes a first nosepiece disposed within a second nosepiece. Nitrous oxide is supplied to the inner nosepiece while a source of vacuum is connected to the region between the first and second nosepieces. The double nosepiece variety of mask is expensive initially and has a high replacement cost. Furthermore, the mask is difficult to keep clean and hard to disassemble; and its four hoses make it cumbersome, uncomfortable to the patient, and obstructive to the operating field of the dentist. Another type of scavenging system is the Allen circuit, made by Dupaco, San Marcos, Calif. The Allen circuit uses a gas reservoir and pressure demand valves to recirculate exhaled gases. This type of system is expensive, as it requires elaborate valving and gas controls. Another type of scanvenging mask, offered by Frazer Sweatman, Inc. Lancaster, N.Y. uses a constant flow gas supply connected to a nosepiece and a pressure operated one-way exhaust valve. When the nosepiece gas pressure rises above a predetermined level, the exhaust valve opens to scavenge gases. In a mask of the latter type, gas tends to leak out the edges because the nosepiece is pressurized. None of the previously available scavenging masks described above are effective in scavenging gas exhaled through the patient's mouth.

SUMMARY OF THE INVENTION

The present invention provides a scavenging mask apparatus for administering gas to a patient, wherein lost and exhaled gas is scavenged by vacuum means. In one embodiment, the invention comprises: a nosepiece adapted to fit over the patient's nose and shaped to form a seal between the rim of the nosepiece and the patient's face; means for connecting the nosepiece to a source of vacuum; a nasal cannula disposed inside the nosepiece and attached thereto; and means for connecting the cannula to a source of gas. The constant flow of gas entering the cannula is delivered directly to the patient's nostrils. Any gas escaping from the cannula, as well as gas exhaled through the nostrils, is scavenged by the continuous air flow inside the nosepiece and swept toward the source of vacuum. A plurality (one or more) of holes in the underside of the nosepiece breaks the vacuum, allowing air flow for scavenging gas exhaled through the patient's mouth. The holes also prevent the mask from locking onto the patient's face due to suction.

A second embodiment further includes pressure demand valve means, air dilution means, and means for effecting a seal between the nostril tubes and the patient's nares. The pressure demand means provides for gas flow when the patient inhales. Gas supply to the mask is therefore intermittant, conserving nitrous oxide. When the patient exhales, the continuous air flow scavenges gas from inside the nosepiece.

The present invention provides a high scavenging efficiency because of the relatively large volume inside the nosepiece as compared to the volume of the nasal cannula. Also, the slight suction effect tends to hold the nosepiece against the face, maintaining the integrity of the seal between the nosepiece and the face.

Accordingly, an object of the present invention is to provide a gas scavenging mask that has a high scavenging efficiency and scavenges gas exhaled from the nose and mouth of the patient.

A further object of the invention is to provide a gas scavenging mask that is inexpensive, easy to clean and easily connected to commonly available gas equipment.

A further object of the invention is to provide a gas scavenging mask that is small, lightweight and comfortable to wear.

Other objects of the invention, and advantages thereof, will become clear from reference to the detailed description and the accompanying drawings.

BRIEF DESCRIPTION OF THE DRAWINGS

FIG. 4 is a cross-sectional view of the second embodiment, employing pressure demand means and air dilution means.

FIG. 5 is a detailed drawing of the air dilution means.

FIG. 6 is a cross-sectional view of the air dilution means.

FIG. 7 shows the valve discs and their relationship to the patient's nose.

DETAILED DESCRIPTION

Figure 1:
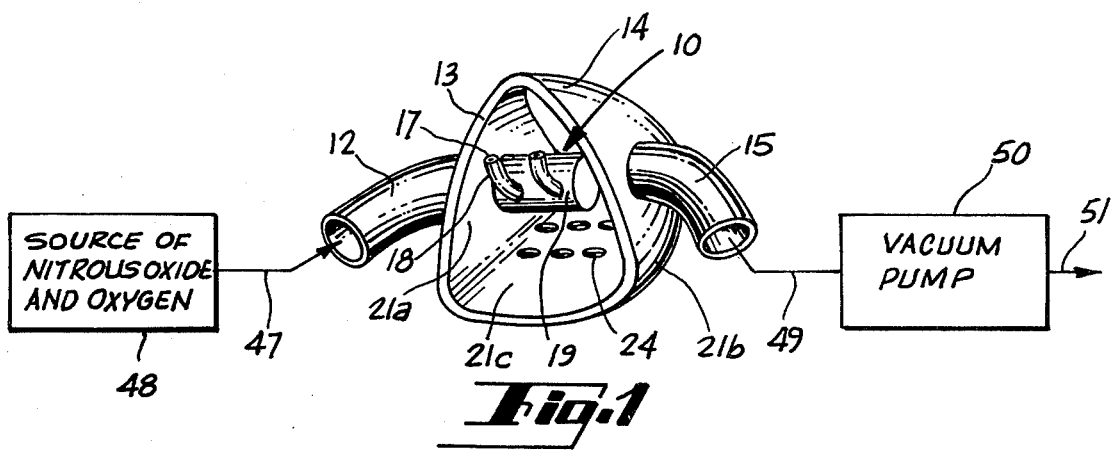
FIG. 1 shows the assembled nosepiece and cannula, viewed from the wearer's position.

The assembled invention shown in FIG. 1 is comprised of four major elements: a nosepiece 14, a cannula 10, first conduit means 12 for introducing gas into the cannula through a lateral wall 21a of the nosepiece, and second conduit means 15 for exhausting gas from the nosepiece through the other lateral wall 21b thereof.

The nosepiece 14 is a cup-like structure of soft, flexible material designed to fit over the patient's nose, and shaped so that the rim 13 of the nosepiece 14 fits the contour of the patient's face. The underside 21c of the nosepiece 14 is formed with a plurality of holes 24 therethrough. When the mask is worn, the holes 24 in the underside 21c are disposed just above the patient's mouth.

Inside the nosepiece 14 is a nasal cannula 10, removablattached to one lateral wall 21a. Generally, a nasal cannula is any one of a variety of small tube means leading into a patient's nostrils for the purpose of administering gas thereto. In the present invention, the nasal cannula 10 is a tubular body 19 open at one end and closed at the other, and a pair of nostril tubes 18 in flow communication at the proximal end thereof with the tubular body 19. When the mask is worn, the distal ends 17 of the nostril tubes 18 are disposed at or inward of the patient's nares. The cannula 10 and nostril tubes 18 are made of soft, pliable material that can be adjusted to the patient for a comfortable fit.

The cannula 10 is removable, as hereinafter discussed, so that the mask may be easily cleaned. Also, since the cannula can be made of relatively inexpensive plastic, it can be disposable and a fresh cannula installed for each patient.

Conduit means 12, an integral extension of the lateral wall 21a of the nosepiece, conduits gas through the nosepiece and into the cannula 10. Inside, the nosepiece connector tube 30 (FIG. 3 and FIG. 4) holds the cannula in place. The connector tube 30 is a rigid tube formed with a ferrule on each end 29, 31. The ferrule ends 29, 31 of the conductor tube 30 have peripheral ridges slightly larger than the inner diameter of the gas conduit means 12 so that a seal is effected when the ferrule end of connector tube is press fitted into the conduit means 12. The conduit means 12 is made of a soft, flexible material that will hold the connector tube 30 in place when it is inserted therein.

To assemble the cannula to the nosepiece, the connector tube 30 is inserted part way into the conduit 12 from the inside of the nosepiece. The cannula 10 is slipped over the exposed ferrule end 31 (FIG. 3 and FIG. 4) of the connector tube 30 and adjusted to a position for engaging the nostrils of the wearer. Thus, the conduit means 12 is in flow communication with the connector tube 30, which is in flow communication with the cannula 10.

In use, the mask is connected to a conventional source of nitrous oxide and oxygen mixture 48 and a conventional source of vacuum 50 (FIG. 1). A supply tube 47 connects pressurized gas from said gas supply 48. A source of vacuum 50, which can be the central vacuum system often found in dental offices, is connected to conduit 15 via a suitable tube 49.

Figure 2:
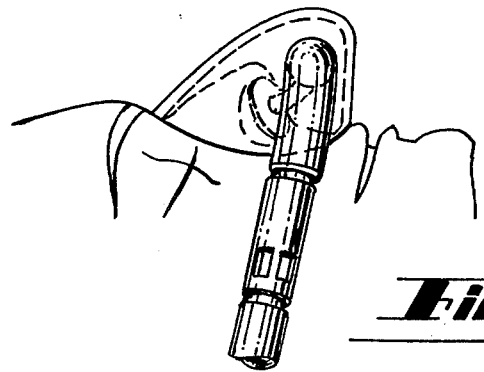
FIG. 2 shows a patient wearing the mask in place over the nose.

The mask is placed over the nose of the patient as shown in FIG. 2 and secured by a strap means or the like (not shown). Gas from source 48 is conducted into the cannula 10 through the lateral wall 21a of the nosepiece 14 via supply tube 47 and delivered to the patient's nares.

When the patient inhales, gas from source 48 is supplemented by air drawn through holes 24 in the underside of the mask. When the patient exhales, the vacuum-induced flow inside the nosepiece scavenges exhaled gases via tube 49 toward the vacuum pump 50 and to an external dump via tube 51. Lost gas, defined as gas from the cannula 10 that is not inhaled, is similarly scavenged. Gas exhaled from the mouth is scavenged by vacuum flow through the holes 24 in the underside 21c of the mask.

Figure 3:
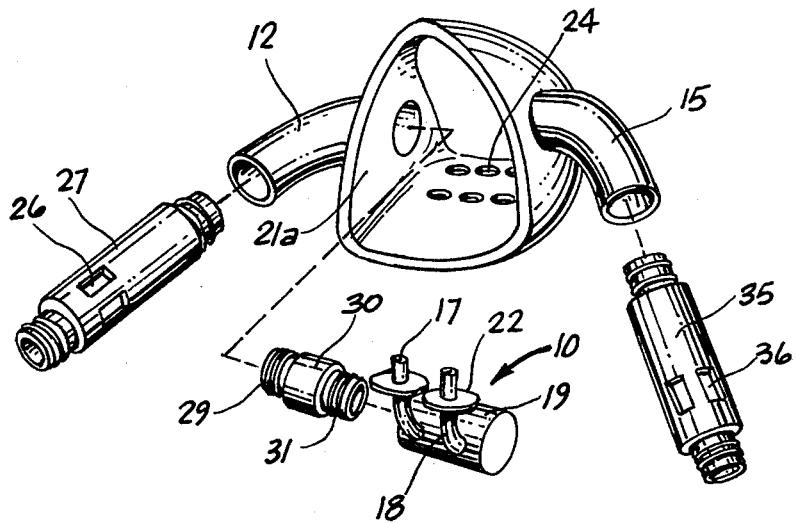
FIG. 3 is an exploded perspective view of a second embodiment, employing pressure demand means and air dilution means.

As described above, this embodiment provides a constant gas flow for supply and a constant vacuum flow for scavenging exhaled and lost gas. A second embodiment, having an intermittent gas flow to conserve nitrous oxide, is shown in FIG. 3. Whereas in the first embodiment nitrous oxide is supplied continuously, in the second embodiment oxide is supplied only during inhalation.

As shown in FIG. 3, the second embodiment further comprises a cannula 10, including a pair of flutter discs 22, and a valve 27, including pressure demand means and air dilution means. The construction and operation of this embodiment of the invention may be more clearly understood by reference to the cross-sectional view of FIG. 4.

The flutter valve discs 22 are concentrically mounted on the nostril tubes 18 near the distal end thereof so that when the mask is worn the discs are positioned at or near the patient's nares. The flutter discs 22 are made of soft, flexible material that is easily deflected by the movement of gases, but rigid enough to retain their disc shape when there is no gas movement. The operation of the flutter valve discs 22 will become clear below.

In series with the conduit means 12 for supplying gas is a valve 27, comprising pressure demand means and air dilution means. Both functions are contained in a single valve unit 27. The pressure demand means further includes a circular seal 45, a ball 39 of a size to seat in the circular seal and a spring 40 for resiliently urging the ball against the circular seal. Also included is a means for adjusting the tension in the spring 40 to set the predetermined value of gas pressure at which the pressure demand valve will open. Said adjusting means includes an end plug 28 with a channel 46 therethrough, the plug being formed with a ferrule on one end and helical grooves 42 on the outside of the other end. Helical grooves on the inside of the valve body 27 match the radius and pitch of the grooves on the end plug so that, as the end plug 28 is rotated about its axis, the plug will advance longitudinally, increasing or decreasing (depending upon the direction of rotation) the tension in the spring 40.

Also provided in the valve 27 is an air dilution means 38. Referring to FIGS. 5 and 6, the air dilution means includes two rectangular openings 26 in the valve body. Covering the openings 26 is a sheet of floppy material 43 attached to a point 44 between the rectangular openings 26. When the gas pressure inside the air dilution means is greater than the gas pressure outside, the floppy sheet 43 flattens against the valve wall, sealing the rectangular holes 26. If the pressure inside is less than the pressure outside (atmospheric), the floppy sheet 43 collapses inward, allowing air to enter the valve 27 through the holes 26.

On the vacuum supply side of the nosepiece, a fitting 35 may be used in series with the conduit means 15. The fitting has holes 36 in the body thereof to break the vacuum so that an air flow is maintained at all times.

In operation, the apparatus is connected to a source of nitrous oxide and oxygen 48 and to a source of vacuum 50 (FIG. 1) as previously described. The mask is placed over the patient's nose, against the face, and secured thereto by any suitable strap means. The distal end 17 of the nostril tubes 18 are disposed just inside the nostrils, and the flutter discs 22 are disposed just at or very close to the patient's nares.

When the patient is not inhaling, the pressure demand valve means is closed. Air flows toward the vacuum source from holes 24 in the underside of the mask and through conduit 15.

When the patient inhales, the flutter valve discs 22 deflect toward the nares, forming a seal between the nostril tubes 18 and the patient's nares. Inhalation reduces the gas pressure inside the cannula 10. When the gas pressure in the cannula 10 falls below a predetermined value, the pressure demand valve will open, allowing the flow of fresh gas to the patient. As shown in FIG. 4, the pressure demand valve will open when the gas pressure in the air dilution chamber 38 is great enough to push the ball 39 out of its seal 45 and compress the spring 40. Gas flows from the supply 48 through the valve means 27, the conduit means 12, the connector tube 30, and into the cannula 10. As previously discussed, the predetermined value of gas pressure at which the valve will open is adjustable by rotating the end plug 28. If patient demand for inhalation is great enough, the air dilution means will open, mixing atmospheric gases with the gas supplied to the patient.

When the patient exhales, the pressure demand valve means closes. The flutter discs deflect to allow gases to be exhaled from the patient's nose into the nosepiece where the vacuum flow scavenges such exhaled gas out of the nosepiece. Gases exhaled through the mouth will be scavenged by the vacuum flow through holes 24 in the underside of the nosepiece.

While this invention is intended for administering gaseous analgesia, such as nitrous oxide, it will be obvious that it may be used to deliver other gaseous analgesia, anesthesia, or gaseous medication administered for purposes of medical or dental treatment. Furthermore, the invention may be embodied in yet other specific forms without departing from the spirit or essential characteristics thereof. Accordingly, the present embodiments are to be considered in all respects as illustrative and not restrictive, the scope of the invention being indicated by the appended claims.

What is claimed is:

1. A scavenging mask apparatus for administrating gas to a patient and for scavenging exhaled gas and lost gas via a source of vacuum to an external point remote from said patient, the apparatus comprising:

A. a cup-like nosepiece arranged to fit over the patient's nose, the nosepiece shaped to form a seal between the rim of the nosepiece and the patient's face;

B. A nasal cannula, disposed within and attached to the nosepiece, for delivering gas to the patient's nostrils;

C. first conduit means connected to the nasal cannula for directing gas through the nosepiece, into the nasal cannula, and to the patient's nostrils; and D. second conduit means connected to the nosepiece and to said source of vacuum for conducting gas so that exhaled gas and lost gas inside the nosepiece is conducted therefrom to said external point through the second conduit means, wherein said first conduit means is a tubular extension integral to and extending outwardly from one lateral wall of said nosepiece, said second conduit means is a tubular extension integral to and extending outwardly from the opposite lateral wall of said nosepiece, and said nasal cannula comprises:

a. a connector tube, open at both ends and formed with a ferrule on each end thereof, the connector tube releasably communicating at one end thereof with the first conduit means;

b. a tubular body having an open end and a closed end, the tubular body releasably communicating at the open end thereof with the other end of the connector tube; and c. two nostril tubes, spaced apart and disposed in the patient's nose at the distal ends of each tube, and communicating with the tubular body at the proximal ends of each tube so that gas entering the tubular body from the connector tube flows to the nostril tubes and into the patient's nostrils.

2. A system for administering gas to a patient, the system comprising:

A. a mask comprising:

a. a cup-like nosepiece arranged to fit over the patient's nose, the nosepiece shaped to form a seal between the rim of the nosepiece and the patient's face;

b. a nasal cannula, disposed within and attached to the nosepiece, for delivering gas to the patient's nostrils;

c. first conduit means connected to the nasal cannula for directing gas through the nosepiece, into the nasal cannula, and to the patient's nostrils; and d. second conduit means connected to the nosepiece for conducting gas so that exhaled gas and lost gas inside the nosepiece is conducted therefrom through said second conduit means;

B. means connected to the first conduit means for supplying gas; and

C. means connected to the second conduit means for supplying a vacuum so that exhaled gas and lost gas is conducted away from the nosepiece, wherein said first conduit means is a tubular extension integral to and extending outwardly from one lateral wall of said nosepiece, said second conduit means is a tubular extension integral to and extending outwardly from the opposite lateral wall of said nosepiece, and said nasal cannula comprises:

1. a connector tube, open at both ends and formed with a ferrule on each end thereof, the connector tube releasably communicating at one end thereof with the first conduit means;

2. a tubular body having an open end and a closed end, the tubular body releasably communicating at the open thereof with the other end of the connector tube; and 3. two nostril tubes, spaced apart and disposed in the patient's nose at the distal ends of each tube, and communicating with the tubular body at the proximal ends of each tube so that gas entering the tubular body from the connector tube flows to the nostril tubes and into the patient's nostrils.

3. A scavenging mask apparatus for administering gas to a patient, and for scavenging exhaled gas and lost gas via a source of vacuum to an external point remote from said patient, the apparatus comprising:

A. a cup-like nosepiece arranged to fit over the patient's nose, the nosepiece shaped as to form a seal between the patient's face and the rim of the nosepiece;

B. a nasal cannula, disposed within and attached to the nosepiece, for delivering gas to the patient's nostrils;

C. first conduit means connected to the nasal cannula for directing gas through the nosepiece, into the nasal cannula, and to the patient's nostrils;

D. pressure demand valve means in flow communication with the first conduit means for conducting gas thereto whenever gas pressure in the nasal cannula falls below a predetermined value;

E. air dilution means in flow communication with the pressure demand valve means for conducting gas to the pressure demand valve means, and for diluting the conducted gas with air whenever gas pressure in the air dilution means falls below atmospheric pressure; and F. second conduit means connected to the nosepiece and to said source of vacuum for conducting gas so that exhaled gas and lost gas inside the nosepiece is conducted therefrom to said external point through the second conduit means, wherein said nosepiece further includes a plurality of holes in the underside thereof; and the nasal cannula comprises:

a. a connector tube, open at both ends and formed with a ferrule on each end thereof, the connector tube releasably communicating at one end thereof with said first conduit means;

b. a tubular body having an open end and a closed end, the tubular body releasably communicating at the open end thereof with the other end of said connector tube;

c. two nostril tubes, spaced apart and disposed in the patient's nose at the distal ends of each tube, and communicating with the tubular body at the proximal ends of each tube so that gas entering the tubular body from the connector tube flows to the nostril tubes and into the patient's nostrils; and d. seal means attached to said nostril tubes for effecting a seal between said nostril tubes and the patient's nares during inhalation.

4. Apparatus according to claim 3, wherein said seal means comprises:

two flutter valve discs of soft, flexible material concentrically attached to the nostril tubes near the distal ends thereof, and disposed adjacent to the patient's nostrils so that said discs form a seal between the nostril tubes and the patient's nares during inhalation of gas.

* * * * *